Figure 1:
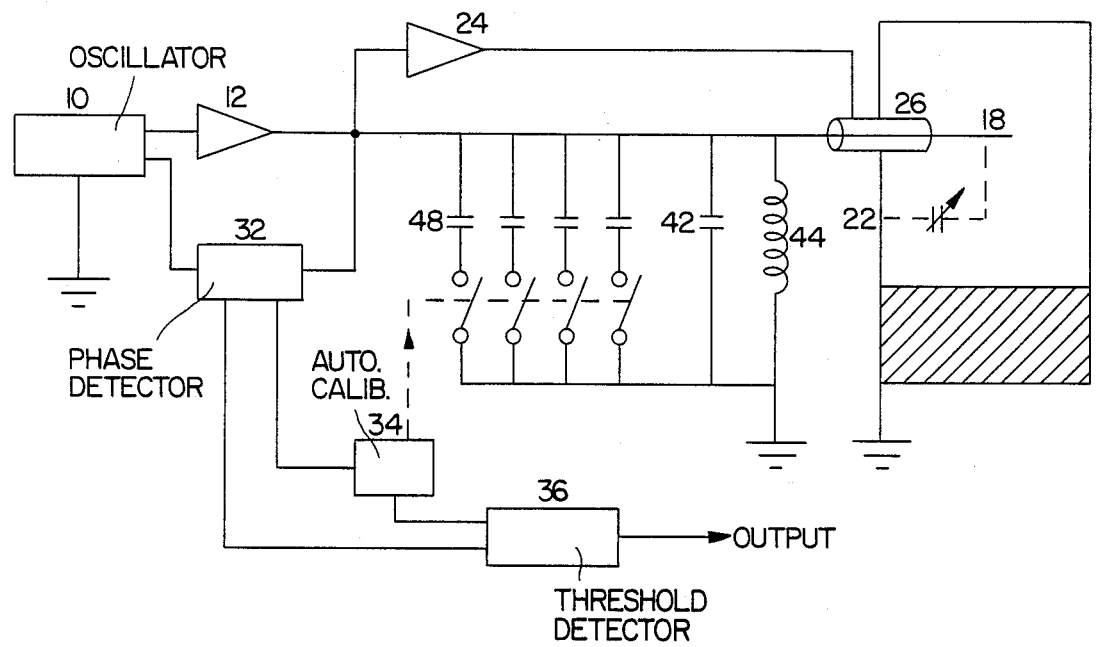
Figure 2:
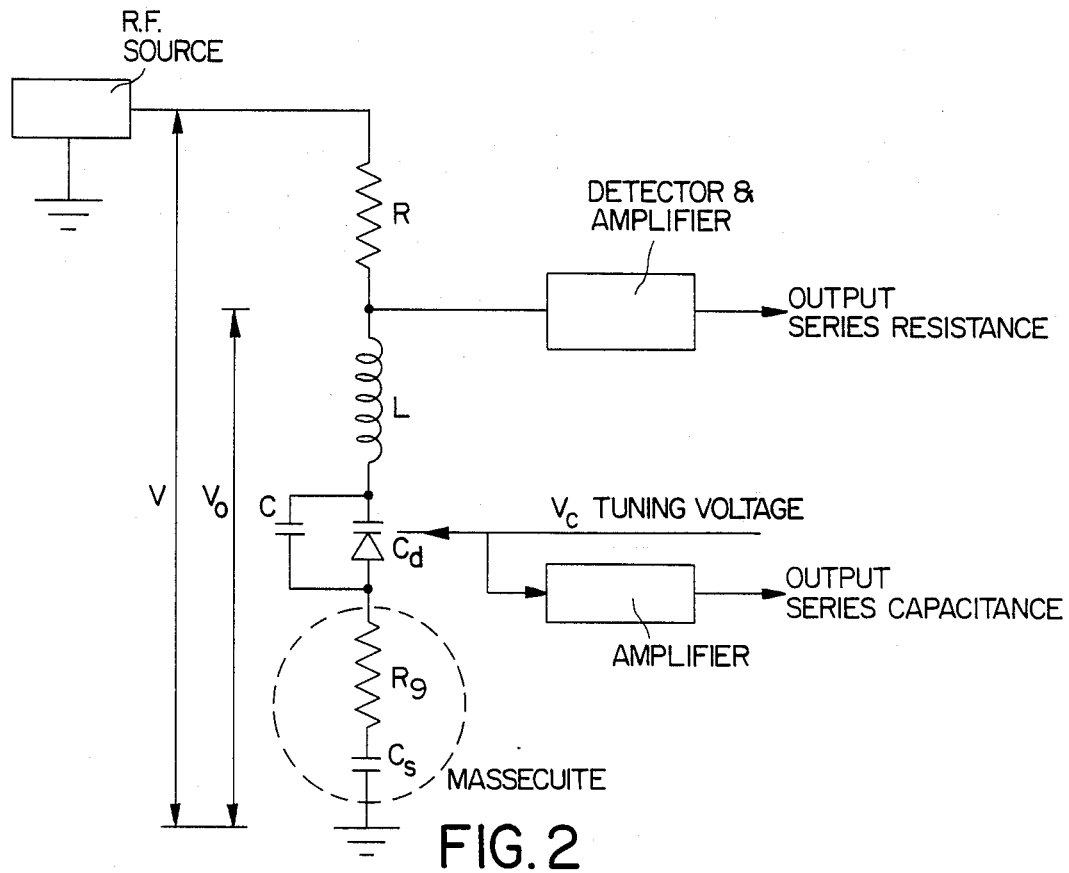

United States Patent [19]

Radford

[11] Patent Number: 4,875,940
[45] Date of Patent: Oct. 24, 1989

[54] MASSECUITE SUPERSATURATION MONITOR

[75] Inventor: David J. Radford, Maidstone, South Africa

[73] Assignee: The Tongaat-Hulett Group Limited, Mount Edgecombe, South Africa

[21] Appl. No.: 161,301

[22] Filed: Feb. 25, 1988

Related U.S. Application Data

[63] Continuation of Ser. No. 724,847, Apr. 18, 1985, abandoned.

[30] Foreign Application Priority Data

Apr. 19, 1984 [ZA] South Africa ............... 84/2976

[51] Int. Cl.$^4$ ............................................. B01J 2/00
[52] U.S. Cl. ........................................ 127/2; 127/9; 127/15; 127/16; 127/17; 324/52 Q; 324/61 R; 324/436; 324/442; 324/443
[58] Field of Search ............... 127/2, 9, 15, 16, 17; 324/57 Q, 61 R, 436, 442, 443

[56] References Cited

U.S. PATENT DOCUMENTS

| | | | |
|---|---|---|---|
| 3,899,386 | 8/1975 | Komiyama et al. | 127/61 |
| 4,196,385 | 4/1980 | Vestergaard et al. | 127/61 |
| 4,468,610 | 8/1984 | Hanson | 324/61 R |
| 4,468,611 | 8/1984 | Tward | 324/61 R |
| 4,547,725 | 10/1985 | Oetiker et al. | 324/61 R |
| 4,549,134 | 10/1985 | Weiss | 324/61 R |
| 4,555,941 | 12/1985 | Fathauer et al. | 324/57 |

FOREIGN PATENT DOCUMENTS

| | | | |
|---|---|---|---|
| 82178 | 5/1986 | Denmark. | |
| 2346411 | 12/1977 | France. | |
| 7739659 | 12/1979 | France. | |
| 2508672 | 12/1982 | France. | |
| 47801 | 1/1978 | U.S.S.R. | 127/16 |
| 589255 | 1/1978 | U.S.S.R. | |

OTHER PUBLICATIONS

"Influence of Controllable Massecuite Properties on Crystallizer Processing and Molasses Exhaustion", Cane Sugar Handbook, 9th Edition, pp. 222 and 223.
"Recent Developments in Pan Boiling Automatics", *International Sugar Journal*, vol. 86, No. 1023, 1984, by Gunther R. Moller, pp. 73–79.
"The Use of Electrical Properties Measured at Radio Frequencies for Pan Boiling & Brix Control", *Proceedings of the South African Technologists' Association*, Jun. 1986, by D. J. Radford et al., pp. 94–102.

*Primary Examiner*—Asok Pal
*Attorney, Agent, or Firm*—Young & Thompson

[57] ABSTRACT

The invention provides an apparatus for controlling both the supersaturation of the mother liquor and the crystal content of massecuite by measuring di-electric constant and electrical conductivity at radio frequencies by means of a probe which is included in a circuit which may be tuned to a fixed setting or may be variably tuned, the combined impedance is measured as a function of the tuning and the measurements are compared with predetermined desired values. By suitable combination of the two signals, measurement of crystal content and mother liquor supersaturation can be controlled.

1 Claim, 1 Drawing Sheet

MASSECUITE SUPERSATURATION MONITOR

This application is a continuation of application (Ser. No. 724,847, filed Apr. 18, 1985, now abandoned.

PRIOR ART STATEMENT

The only relevant prior art known to the Applicant is French Patent 77/39659 (Danske Sukkerfab) in which the di-electric constant of a solution are measured by means of a probe and the strength of the signal returned from the probe is compared to that returned under known conditions of concentration.

FIELD OF THE INVENTION

This invention relates to a sugar vacuum pan control system.

BACKGROUND TO THE INVENTION

In the past, the control of vacuum pan boiling has always been made difficult by the fact that no simple means existed for the direct measurement of supersaturation and crystal content in massecuites. These are the two prime variables to be controlled and until they can be measured, it is not possible to achieve optimal control of vacuum pan boiling. In the past, measurement of conductivity, viscosity, elevation of boiling point, density and dielectric constant have been used with various degrees of success to control vacuum pans.

In raw sugar factories, electrical conductivity is the most common of these parameters used for pan control. This measurement, however, suffers from a few serious drawbacks:

(1) The conductivity measurement is very dependent on the purity of the boiling massecuite, particularly when the purity is greater than 85.

(2) The conductivity measurement depends on crystal content and mother liquor purity and brix of the massecuite and it is possible to have two different qualities of massecuite having the same conductivity.

(3) When used in continuous vacuum pans, conductivity probes are subject to extensive scaling, which has a considerable effect on the reading.

It is an object of the present invention to provide a method and apparatus for measuring conductivity and di-electric constant in order to obtain a more exact control of the conditions of massecuite.

THE INVENTION

According to the invention a method of controlling the supersaturation of the mother liquor and the crystal content of massecuite is characterised in that the di-electric constant and electrical conductivity are measured at radio frequencies by means of a probe located in a vacuum pan at a zone of vigorous circulation, and included in a tuned circuit, where the combined circuit impedance is measured as a function of the tuning of the circuit; and by suitable combination of di-electric constant and electrical conductivity, signals representative of massecuite mother liquor concentration and crystal content can be controlled.

In an example of the apparatus according to the invention a probe adapted to measure both the di-electric constant and the electrical conductivity of the massecuite is connected through a tuning circuit such as a series tuned capacitor and inductor network or equivalent arrangement, to an AC bridge circuit or voltage divider network which uses a high frequency signal in the radio frequency range; the output from this circuit being converted to a suitable signal for control instruments, the bridge or voltage divider circuit being calibratable in relation to one or more predetermined values of combined impedance, and means to adjust the conditions of the massecuite in accordance with the difference between the predetermined values and the measured values.

The radio frequency signal may be derived from a stable oscillator such as a crystal controlled oscillator and a buffer amplifier; the output voltage of this amplifier is kept constant by means of a detector and automatic gain control circuit; the output of this amplififer is used to supply the bridge circuit or voltage divider circuit, which includes the probe and tuning circuits; the output from the bridge or voltage divider is rectified, amplified and converted to a signal suitable as an input to control instruments. This latter signal may be of the order of 4–20 milliamps.

In order to calibrate the amplifier and detector circuits, two fixed resistors are switched into the bridge circuit or voltage divider circuit in place of the probe and tuning circuit and gain and offset of the amplifier is adjusted to set span and zero of the measurement circuit. This system is then used to measure the combined impedance of the probe massecuite and the tuning circuit. By adjusting a variable inductor or capacitor in the probe circuit, the circuit reactance can be tuned out. At this point, the probe and the tuning circuit are in resonance at the measurement frequency.

There are two alternatives as to how the probe may be used in conjunction with the series-tuned circuit:

(1) The tuning circuit may be tuned to a fixed setting, so that the circuit, including the measurement path through the massecuite exhibits capacitive or inductive reactance. Under these conditions, the output of the probe will vary according to changes in massecuite impedance, due to changes in massecuite physical properties, for example, crystal content or mother liquor brix.

The fixed tuning may be set to an optimum value. For example, when boiling high grade massecuite in a raw sugar factory, it has been found that if the tuning circuit is adjusted so that the probe and tuning circuit exhibits inductive reactance, then the sensitivity of the instrument to changes in massecuite conditions is greatest. Under these conditions, an increase in crystal content and/or an increase in mother liquor brix, will cause an increase in the output of the instrument and this signal may then be used to control the feed into the vacuum pan.

(2) As an alternative to the above, the probe may be fitted with a means for automatically varying the tuning of the circuit. For example, a varicap diode may be included in the tuning circuit. The output of the instrument may then be fed into a microprocessor, which is programmed to provide an output signal which may continuously vary the tuning of the probe.

The microprocessor may be programmed to continuously adjust the probe to resonance, measure the output signal from the probe at this point and the signal fed to the tuning circuit and from these measurements together with an experimentally determined value of inductance of the measurement path through the massecuite compute the massecuite parallel resistance and capacitance. These two parameters can then be used for pan control in various ways. For example, the capacitance can be used to control crystal content, since it has been found that this parameter is almost independent of mother liquor brix. In effect, having two outputs means that a massecuite can be fixed in quality and various control philosophies can be derived using these two parameters or various combinations thereof to control a vacuum pan.

As an alternative to (2) above, the probe may be designed such that instead of a stable oscillator (for example a crystal oscillator) in the measurement circuit, this could be replaced by a variable frequency oscillator. In this case, the probe tuning may be fixed and the variable frequency oscillator may be controlled by the microprocessor. The microprocessor may be programmed to continuously adjust the probe to resonance as before, by varying the frequency of the oscillator and from a measurement of probe output at resonance and the frequency of the oscillator, the massecuite parallel capacitance and resistance may be calculated as before.

The fact that massecuite capacitance or di-electric constant and resistance can be measured independently, means that this probe can be used for controlling high or low grade pans.

The probe can be insulated or non-insulated from the massecuite. In the case of the probe being insulated, calibration is very difficult and therefore, a noninsulated probe is preferred. Calibration and setting-up of the probe is carried out by connecting resistor capacitor combinations across the probe. An additional inductor and variable capacitors in the probe-tuning circuit allows standardisation of individual probe calibration.

Apart from its other advantages, the present invention is less prone to the effects of fouling than conventional conductivity electrodes. Usually fouling of the probe results in inaccurate measurement after a short period of time in massecuites of high purity, but with the present arrangement, it is only when severe fouling takes place that the outputs may be significantly displaced. This makes this type of probe particularly suitable for use in continuous pans. Typically, a probe may operate for periods of one week without the necessity for cleaning in a high grade continuous pan.

EMBODIMENT OF THE INVENTION-BRIEF DESCRIPTION OF DRAWING

An embodiment of the invention is illustrated in the accompanying circuit diagram in which a probe 10 is connected to a tuning circuit 12, whose output passes through a detector and amplifier 14 to a microprocessor controller 16 having outputs 18 and 20 for adjusting the probe to resonance and to control pan parameters in any desired manner.

The radio frequency generator circuit generally includes an RF oscillator 32, and a detector and AGC 34 both connected to a buffer amplifier 36 to control the output voltage fed to resistor R. Resistor R, the probe and tuning circuit constitutes the voltage divider network which could alternatively be replaced by a bridge type network.

I claim:

1. Apparatus for controlling the supersaturation of a mother liquor and the crystal content of massecuite comprising:
    (a) probe means adapted to continuously measure both the series resistance and the series capacitance of the massecuite, said probe means being located in a vacuum pan at a zone of vigorous circulation;
    (b) a voltage divider including a resistor in series with a series tuning circuit and said probe means, said voltage divider being supplied with a signal in the radio frequency range to create an output signal;
    (c) converter means for converting the output signal from the voltage divider to a suitable signal to be used by control instruments;
    (d) calibration means for calibrating the output signal from the voltage divider;
    (e) first control means to continuously keep the probe and tuning circuit in resonance;
    (f) measuring means to measure both the impedance of the probe and tuning circuit at resonance and changes in capacitance necessary to keep the circuits in resonance;
    (g) calibrating means to calibrate the probe and tuning circuits such that the absolute values of massecuite resistance and capacitance can be measured; and
    (h) second control means to derive optimum signals for control of crystal content, and mother liquor Brix using the calibrated probe output signals.

* * * * *